Figure 1:
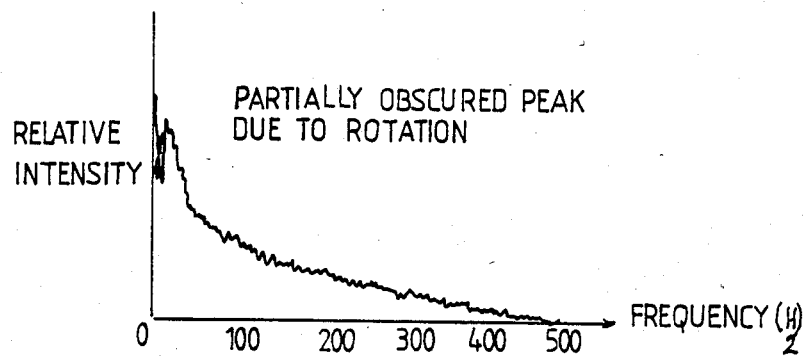

United States Patent [19]
Woolhouse et al.

[11] Patent Number: 4,601,578
[45] Date of Patent: Jul. 22, 1986

[54] MEASUREMENT OF SPERM MOTILITY

[76] Inventors: James K. Woolhouse, 5 Bellwood Pl., Chedworth, Hamilton; Murray W. Woolford, 57 Berkley Ave., Hillcrest, Hamilton, both of New Zealand

[21] Appl. No.: 497,672

[22] Filed: May 24, 1983

[30] Foreign Application Priority Data

May 25, 1982 [NZ] New Zealand .................. 200732

[51] Int. Cl.$^4$ .......................................... G01N 21/49
[52] U.S. Cl. ................................................ 356/338
[58] Field of Search ..................... 356/338, 337, , 340, 356/341, 342, 343

[56] References Cited

PUBLICATIONS

Naylor et al., Apparatus for the Study of Motile Sperm Using Microprocessor Analysis of Scattered Laser Light, Med, & Biol. Eng. & Comput., 20, 207–214 (Mar. 1982).
Jouannet et al., Light Scattering Determination of Various Characteristic Parameters of Spermatozoa Motility in a Serie of Human Sperm, Andrologia 9(1), 36–49 (1977).

Primary Examiner—John Kittle
Assistant Examiner—Thomas C. Saitta
Attorney, Agent, or Firm—Holman & Stern

[57] ABSTRACT

A micro-sample of semen is exposed to a beam of light from an inexpensive and small laser device. Light scattered by the sample is detected by a photodetector. The photodetector signal is analyzed in the frequency domain to provide a measure of the amplitude of the signal components having frequencies above about 100 Hz. This measure is representative of the numbers of motile sperm in the sample. A motile/immotile percentage is obtained by dividing the motile measurement by a value representative of the amplitude of the full-frequency photodetector signal. In a preferred embodiment frequency-amplitude analysis is carried out in the time domain using frequency splitting filters and integrating the filtered signals. The light receiving aperture for the photodetector is made annular or part-annular in shape to overcome sample orientation or polarization effects.

9 Claims, 8 Drawing Figures

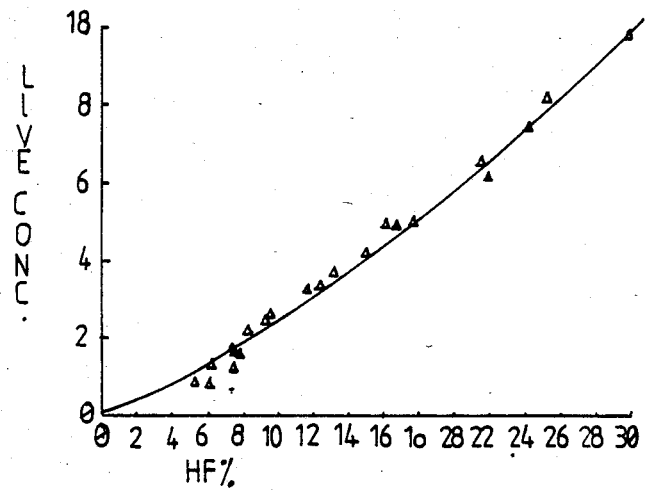
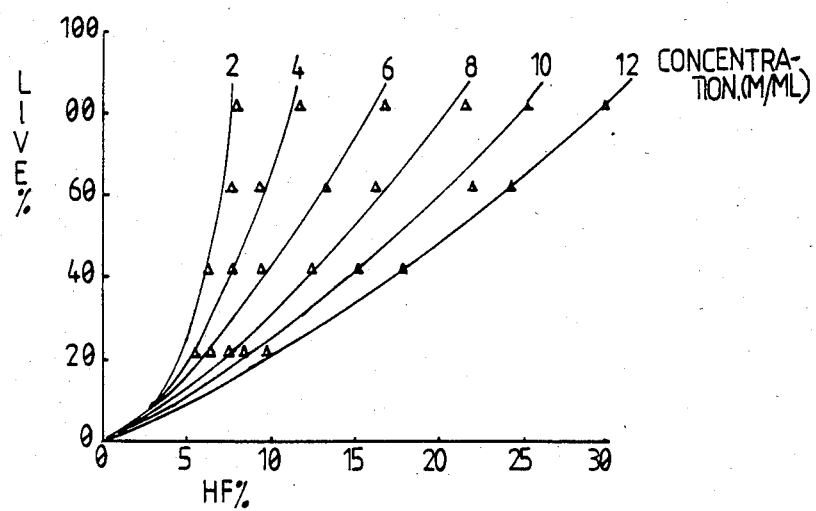

MEASUREMENT OF SPERM MOTILITY

This invention relates to the measurement of sperm motility with particular application in the area of artificial insemination.

Artificial insemination is a widely used technique in the selective breeding of animals, particularly dairy cattle. The success of any artificial insemination programme is dependent on the availability of semen of high quality. Having selected sires on genetic merit, the most important factor in assessing semen quality is sperm motility, that is, the forward progression of individual spermatoza in suspension. Motility should be assessed before storage in a sperm bank and then again before distribution. Until recently there has been no reliable or effective method of assessing sperm motility.

Two methods commonly used in the past to gauge sperm motility are high speed photography and subsequent subjective film analysis and the use of a visual inspection of a semen sample using a graticule and stop watch technique. More recently laser spectroscopy together with subsequent computer analysis has been used to yield estimates of live/dead sperm ratios, concentration measurements, the distribution of head rotation rates and the distribution of forward velocities. The use of a laser as described has resulted in short measurement times, non-destructive assay, excellent statistical data and requires only a micro sample of semen. However such equipment is very expensive, non portable and provides more information than is needed for routine work associated with practical artificial insemination.

It is therefore an object of the present invention to provide a method and apparatus for assessing sperm motility which makes use of the knowledge gained from the laser technique referred to above but which overcomes the mentioned disadvantages.

It has been discovered that laser light scattered from a semen sample contains information indicative of the motility of the sperm contained in the sample, not by virtue of the moving sperm causing Doppler shifts in the light frequency, but by virtue of the flat sperm heads simulating mirrors which rotate at a rate proportional to sperm motility. The scattered laser light can be considered as comprising a composite of flashes of light reflected from the heads of rotating sperms contained within the sample. It has thus been discovered to be unnecessary to use high quality lasers with their necessarily large bulk which restricts their use to a specialised laser laboratory.

It has also been discovered that sperm motility information is contained in the signal produced by a photosensor detecting laser light scattered from a semen sample in such a way that relative signal amplitudes in the time domain are indicative of sperm numbers and relative frequency regimes are indicative of active of inert sperm.

Accordingly in one aspect the invention consists in a method of assaying the motility of sperm in a semen sample comprising:

locating said sample in a temperature controlled optical cell, illuminating said sample with a laser beam, receiving a portion of the light scattered from said sample with a photodetector, measuring the amplitude of the frequency components of the signal above about 100 Hz, measuring the amplitude of the full-spectrum signal and determining the ratio of the high frequency measurement to the full-spectrum measurement to provide a measure of the percentage of motile sperm in said sample.

In a second aspect the invention consists in apparatus for assaying the motility of sperm in a semen sample comprising:

a temperature controlled optical cell in which said sample is held in use, a laser device which projects a beam of light at said sample, a photodetector which receives a portion of the light scattered from said sample, first means for measuring the amplitude of the frequency components of the signal above about 100 Hz, second means for measuring the amplitude of the full spectrum signal, and means which enable the ratio of the values measured by said first and second amplitude measuring means to be produced which is representative of the percentage of motile sperm in said sample.

The present invention provides a technique by which the photodetector signal is analysed in the frequency domain to provide information on the ratio of live to dead sperm in the assayed sample, based on the inventors' discovery that the amplitude of the low frequency and the high frequency components of the photodetector signals are a function of the numbers of dead and live sperm respectively.

Figure 2:
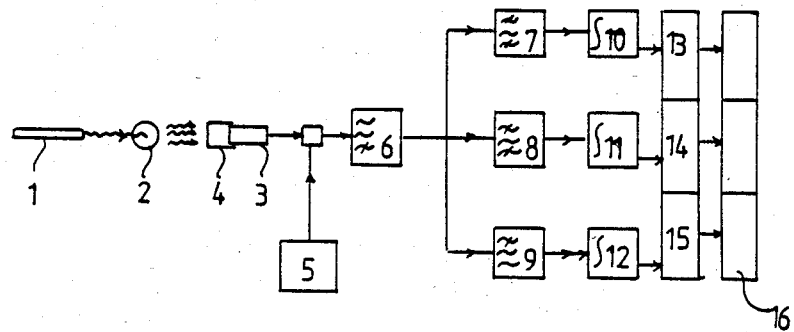
Figure 3:
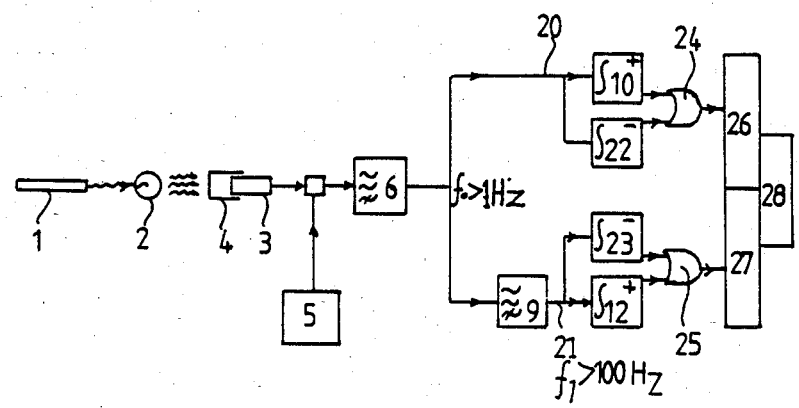
Figure 4:
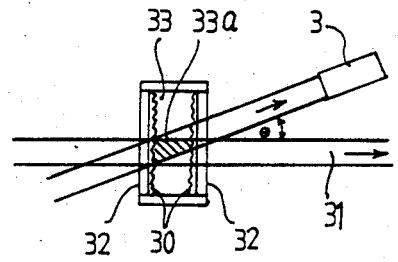
Figure 5:
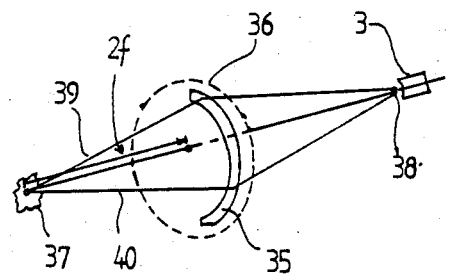

The preferred form of the invention will now be described with reference to the accompanying drawings in which:

FIG. 1 is a power spectrum of a photo-multiplier signal formed by a live/dead suspension of sperm cells scattering incident laser light, FIG. 2 is a block diagram of a first form of sperm analyser, FIG. 3 is a block diagram of a second form of sperm analyser, FIG. 4 is a diagrammatic representation of a sperm sample chamber, FIG. 5 is a diagram of the photodetector optics including a novel aperture.

Figure 8:
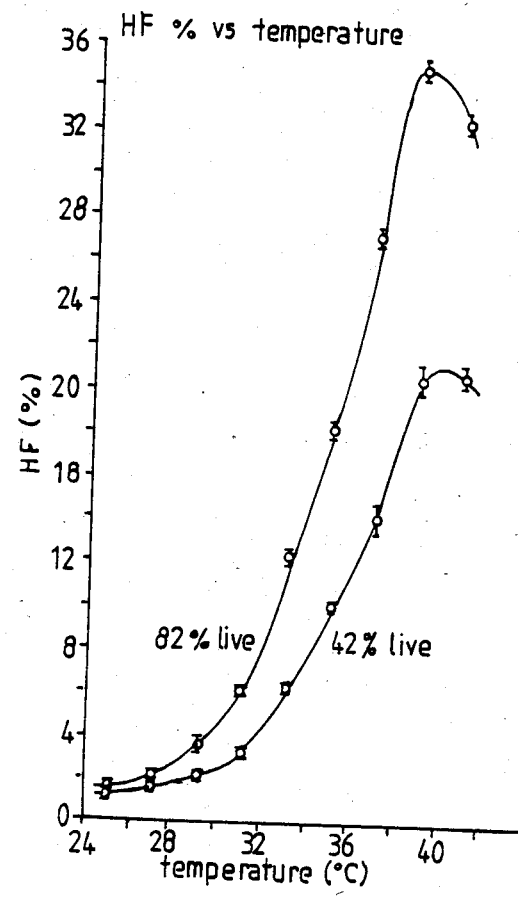

FIG. 6 is a graph of live sperm numbers against the instrumental index for the analyser produced from samples of different total sample concentrations, FIG. 7 is a graph of percentage live sperm against the instrumental index for the analyser produced from samples of different total sample concentrations, and FIG. 8 is a graph of instrumental index readings for two samples showing the effect of temperature on motility.

As has already been mentioned a suspension of motile and non-motile sperm scatters an incident laser beam by virtue of the disc-like sperm heads acting as tiny mirrors and producing flashes of light at a receiving point such that the output of a photomultiplier for example will contain two frequency regimes due to the two different frequencies of rotation of dead and live sperm. Diffusing dead cells rotate, generating photodetector signal frequencies in the order of a few hertz whereas rotating and translating live cells generate signal frequencies in the hundreds and perhaps thousands of hertz. The two sub-spectra produced by dead and live sperms respectively differ markedly in mean frequency but overlap. The live sperm fraction generates an exponential shaped frequency spectrum with a tail extending towards the kilohertz range while the dead fraction generates a Lorentzian frequency spectrum extending from less than 1 Hz up to about 100 Hz (for practical purposes). Complex analysis has been carried out by the inventors in the time domain by autocorrelating the signal produced by a photomultiplier, but such techniques are not suitable for relatively inexpensive and portable equipment. Information equivalent to that contained in the autocorrelated signal is contained in the frequency domain as indicated in the power spectrum of the photomultiplier signal shown in FIG. 1. This power spectrum was produced using direct signal sampling by a computer in association with fast Fourier transform signal processing.

In order to inexpensively evaluate the photomultiplier or other photosensor signal spectrum the present invention preferably splits the output signal into at least two frequency bands and integrates the signals with respect to time so as to provide a reasonable measure of the amplitude of the frequency spectra due to the dead and live sperms respectively. Such an integration technique does however require an accurately determined average or DC signal level. Establishing such a level is a significant problem since there are very low frequency components in the photosensor signal. Frequencies as low as 0.01 hertz are generated by dead sperm exhibiting rotational diffusion through the laser beam. Consequently integration over a long period of time is required before the DC value can be determined and this does not allow rapid or short term changes in sperm activity to be followed. This problem has been overcome by making use of the fact that the signal components below 1 hertz (less than 1% of the total) are common to the spectra of both live and dead sperm and consequently their omission does not significantly affect the ratio of the two spectra. Accordingly a high pass master filter with a cut-off frequency of about 1 hertz follows the photodetector so as to exclude such low frequency components from the main filter-integration network. This cut-off frequency could be varied.

A first embodiment of the sperm motility analyser will be described with reference to FIG. 2. An inexpensive and physically small laser device 1 (typically 5 mW output power) via an associated optical path directs coherent light at a temperature controlled optical cell 2 which contains a micro sample of dilute semen. The cell is normally maintained at body temperature. A photomultiplier or phototransistor 3 receives light reflected from the semen sample through an aperture 4. A programmable timer 5 gates the output of the photosensor 3 to the master filter 6 referred to in the previous paragraph. Timer 5 allows the measurement time to be accurately determined and a time of 300 seconds would be typical for an assay to provide the live/dead sperm ratio of the semen. The gated signal is passed through the master filter 6 to remove frequency components below 1 hertz and this filtered signal is split into three frequency bands by applying it to three elliptic filters 7, 8 and 9. Equiripple elliptic functions were chosen as a result of previous research using autocorrelation analysis which indicated that motility information is present in the amplitude of the spectral components regardless of any phase relationship and accordingly band splitting filters could be chosen on high attenuation and sharp cut-off criteria rather than on phase, delay, or transient merits. The choice of the cut-off frequencies, that is the boundary frequencies between the pass bands of the filters 7 and 8, and 8 and 9 respectively, were determined on the basis of experimental data on the basic two sub-spectra signal. These are 20 hertz and 100 hertz respectively. The power spectra of the live and dead sperm fractions overlap and cannot be separated. The value of the 20 hertz boundary frequency was chosen so that the overlapping portions of the live and dead frequency components were cancelled on taking their ratio. The upper boundary frequency (100 hertz) was chosen because it was known that approximately 15% of the power in a typical photosensor spectrum is above 100 hertz and this arises essentially from the live fraction alone. The 15% figure was considered adequate to obtain an assessment of the power due mainly to the live fraction alone. The pass band gains of all filters were equalised to unity. Useful results can be obtained with other cut-off frequencies and thos stated here are not critical. They are particularly apt for bull sperm.

The outputs of filters 7, 8 and 9 each feed respective integrators 10, 11 and 12. The integrators are of course being used to obtain an assessment of the amplitude of the spectral components within certain frequency ranges. Each integrator accumulates charge such that with high amplitude signals in the time domain it will more rapidly charge up to a value determined by the integrator time constant than would be the case with signals of lower amplitude in the time domain. Each integrator 10, 11 and 12 has been deliberately designed with the same time constant. When each integrator reaches saturation value it is reset to zero and the resetting pulses are counted in a respective digital counter 13, 14 and 15. The integrators are thus used as pseudo elements and do not produce the value of the integral of each signal per se. The count stored in each counter is proportional to the relative value of the integral of the signal in each frequency regime. Provided the time constant of each integrator is equal and each filter channel is processed for the same time (determined by timer 5) the resultant counts recorded in each frequency channel will be directly related to the relative amplitudes of the high frequency and low frequency photodetector signal components and thus to the number of live and dead sperm in the semen sample. If the time constants of each integrator were different it would be necessary to scale the integrator counts to provide information on the relevant numbers of live and dead sperm.

At the end of the preprogrammed processing time (300 seconds for example) the counts in each of counters 13, 14 and 15 are displayed on any known display device 16 and the fractional count (channel count divided by total count) is calculated either electronically or manually for each channel to provide an index indirectly related to live/dead sperm ratios and activity, sensibly independent of any laser light or signal adjustments. The numerical value of each channel count is arbitrary and is determined by the integrator time constant and the photosensor signal level. However the ratios of the counts displayed remain essentially invariant.

In a second and preferred embodiment of the invention, illustrated in FIG. 3, two signal processing channels are used instead of three. In addition both the positive and negative signal components in each channel are integrated. Channel 20 processes the entire signal above 1 Hz while channel 21 processes signal components with frequencies above 100 Hz. The output of channel 20 yields directly a count proportional to the total number of live and dead sperm in the sample, obviating the need to sum the counts from all channels to provide this value for the purposes of determining the percentage of live sperm. The number of integrations is counted by digital counter 26 and may be displayed as such on display module 28 or used as the divisor in an arithmetic unit forming part of unit 28 to produce a "percentage live sperm" display.

As in the first embodiment channel 21 provides a count of integrations of signal components with frequencies greater than 100 Hz which is proportional to the number of live sperm in the sample. This count, stored in digital counter 27 may be displayed directly as such or used as the dividend in the abovementioned arithmetic unit.

Integrators 22 and 23 integrate the negative signal components in channels 20 and 21 respectively. The reset pulses of these integrators are combined with those from the positive signal component integrators 10 and 12 by OR gates 24 and 25 respectively. This has the effect of doubling the statistical significance of data extracted from the photodetector signal. Alternatively the data retrieval time can be halved over that required for the first embodiment of the analyser. Thus a data retrieval time of a few tens of seconds can with this form of analyser provide statistically significant results.

While the first embodiment provides information of use to a researcher whereby the decline of motility with time can be observed by the increase in counts in the two low frequency channels, this information is not required by workers in the field. Accordingly the simplifications realised in the second embodiment do not derogate from the analyser's usefulness in its main intended application.

All the electronic components referred to in the descriptions of the first and second embodiments of the invention are of standard type well known to those skilled in the art and require no special explanation.

The performance of the analyser is evidenced from FIGS. 6 and 7. FIG. 6 shows a graph of live sperm against the quotient obtained from the analyser as a result of dividing the amplitude count from the high frequency channel by the amplitude count from the full frequency (above 1 Hz) channel. This quotient may be termed the instrumental index, HF %. It will be seen from FIG. 6 that the concentration of live sperm is obtained from the instrumental index independent of the total (live and dead) concentration of the sample measured. This graph was produced from measurements on samples having total concentrations of 2, 4, 8 and 12 m/ml.

FIG. 7 shows that the instrumental index also provides the live/dead sperm ratio for samples of different total concentration (2, 4, 6, 8, 10 12 m/ml).

The range of uses to which the instrumental index may be put is exemplified by FIG. 8 which shows variation in instrumental index, HF %, with sample temperature for two sperm populations at 10 million sperm/ml with 82% and 42% (initial) live sperm respectively. Such measurements are useful to provide data on sperm metabolism for example.

The optical cell or sample chamber and the photodetector aperture will now be described. The inventors have discovered that several phenomena within the sperm sample confound the absolute measurement of the ratio of motile/immotile sperm. These are: (1) due to an optical anistropy in the scattering from the sperm head a photodetector with a point aperture to collect scattered light sees only those sperm which have specific directional alignments. If the aperture is located at a point in the plane defined by itself and the laser beam, it collects light only from those cells having longitudional axes oriented within ±20° to the perpendicular to this plane. (2) motile sperm in diluted samples tend to accumulate on the internal surfaces of the sample chamber thus creating a spatially heterogenous sample. The motile sperm swim largely on the surfaces, the immotile sperm remaining distributed uniformly throughout the suspending medium, and (3) immotile sperm, due to a higher specific gravity of the head, sediment head first after orienting to a head down attitude (geotaxis). Thus a horizontally aligned photodetector with a point aperture located at a small forward scattering angle collects light from a significantly larger proportion of immotile sperm than does a vertically aligned detector.

These three factors together with the interactions which occur between motile and immotile sperm result in the motile/immotile ratio being dependent on the concentration of motile cells and render the light scattering measurements empirical unless the concentration effect is corrected for. These problems are at least partially resolved by using a sample chamber of a sandwich type geometry and a photodetector aperture with an annular light collection geometry which collects light from all sperm regardless of orientation.

In FIG. 4, which shows an optical cell or sample chamber, the motile sperm (particularly at high sample dilutions) swim largely on the internal surfaces 30 of the cell. The beam of light 31 from laser 1 is directed through the cell perpendicular to flat polished window surfaces 32. Immotile sperm remain randomly distributed throughout the bulk of the sample volume 33. The photodetector 3 collects forward scattered light from the sperm at an angle $\theta$ (say 10°) with respect to the ongoing laser beam 31. The optics of the photodetector (to be described) are such that light may be received from any point within the illuminated (cross-hatched) region 33a of the sample. The detector therefore sees a sandwich of motile sperm swimming in the illuminated region of the internal chamber surfaces together with the immotile sperm distributed throughout the region 33a in between.

Referring to FIG. 5 to take account of the optical polarisation effect described, the photodetector optics allow collimation of the light by the use of an annular or semi-annular aperture 35 which is mounted coaxial with the scattered laser beam. In FIG. 5, two scattered rays 39 and 40 are shown emanating from the illuminated region 37 and which pass through the semicircular aperture 35 and thence through a focussing lens 36. The image 38 of the illustrated region (scattering volume) is thus formed on photodetector.

This arrangement allows sperm to scatter light to the photodetector 3 regardless of their orientation and allows the photodetector to collect the same level of scattered light regardless of any geotaxis or wall swimming effects.

It should be understood that the signal processing techniques described above are not the only ones which could be used. Other methods of dividing and evaluating the photodetector signal in the frequency domain could be used. For example, digital filters could be used and microprocessor devices used to perform the integration and calculate the ratio of frequency spectra amplitudes. Alternatively microprocessor devices can be used to analyse the signal in the frequency domain using Fourier transform techniques.

We claim:

1. A method of assaying the motility of sperm in a semen sample comprising:
   locating said sample in a temperature controlled optical cell,
   illuminating said sample with a laser beam,
   receiving a portion of the light scattered from said sample with a photodetector,
   measuring the amplitude of the frequency components of the signal above about 100 Hz,
   measuring the amplitude of the full-spectrum signal and determining the ratio of the high frequency measurement to the full-spectrum measurement to provide a measure of the percentage of motile sperm in said sample.

2. Apparatus for assaying the motility of sperm in a semen sample comprising:
   a temperature controlled optical cell in which said sample is held in use,
   a laser device which projects a beam of light at said sample,
   a photodetector which receives a portion of the light scattered from said sample,
   a high pass filter which receives the filtered photodetector signal as an input, a first integrator which integrates the output of the high pass filter; a second integrator with a time constant and saturation level identical to the first which integrates the photodetector signal; each integrator providing as outputs the integrator reset pulses which occur as each integrator reaches saturation; and digital counter means which counts and stores respectively integrator reset pulses in a preselected period to provide counts representative of signal amplitude, said counts being indicative of sperm activity in said sample.

3. Apparatus according to claim 2 wherein a filter substantially removes photodetector signal components with frequencies below 1 Hz and the filtered photodetector signal provides the inputs to said high pass filter and said second integrator.

4. Apparatus according to claim 2 wherein a digital display decodes said counters and displays the number of counts stored in each counter after said preselected period.

5. Apparatus according to claim 2 including an arithmetic unit which calculates the ratio of the counts from the first amplitude deriving means to the counts of the second amplitude deriving means to give a quotient representative of the percentage of motile sperm in said sample.

6. Apparatus according to claim 2 including a band pass filter which receives the photodetector signal and outputs the photodetector signal components having frequencies between about 1 Hz and about 100 Hz, a third integrator with a time constant and saturation level identical to the first integrator which integrates the output of said band pass filter and provides reset pulses to a further counter means, the count in said further counter means being representative of the number of immotile sperm in said sample.

7. Apparatus according to claim 2 wherein the light received by the photodetector is collected by an annular or part-annular light admitting aperture.

8. Apparatus according to claim 7 wherein said optical cell includes two flat glass walls spaced apart in parallel relationship and these walls are aligned perpendicular to the optical path between them and said sample.

9. Apparatus according to claim 2 wherein each integrator comprises:
   two resetting integrating circuits, one adapted to integrate positive polarity signal components and the other to integrate negative polarity signal components;
   and an OR logic gate which combines the reset pulses from each integrating circuit, the output of the integrator being taken from the output of the OR gate.

* * * * *